United States Patent [19]
Karrer et al.

[11] Patent Number: 5,808,143
[45] Date of Patent: Sep. 15, 1998

[54] CATALYST BASED ON OXIDES OF FE, CO, BI AND MO

[75] Inventors: Lothar Karrer, Pfungstadt; Hans-Peter Neumann, Mannheim; Hans-Dieter Eichhorn, Weisenheim am Berg, all of Germany; Robin Stuart Jarret, Cleveland, United Kingdom

[73] Assignee: BASF Aktiengesellschaft, Ludwigshafen, Germany

[21] Appl. No.: 617,792

[22] PCT Filed: Sep. 16, 1994

[86] PCT No.: PCT/EP94/03111

§ 371 Date: Mar. 22, 1996

§ 102(e) Date: Mar. 22, 1996

[87] PCT Pub. No.: WO95/08391

PCT Pub. Date: Mar. 30, 1995

[30] Foreign Application Priority Data

Sep. 24, 1993 [DE] Germany .......................... 43 32 542.4

[51] Int. Cl.$^6$ .............. C07C 5/16; B01J 21/00; B01J 23/00

[52] U.S. Cl. .......... 562/407; 502/202; 502/207; 502/302; 502/303; 502/304; 502/305; 502/306; 502/307; 502/308; 502/310; 502/311; 502/312; 502/313; 502/314; 502/315; 502/316; 502/317; 502/318; 502/319; 502/320; 502/321; 502/322; 502/323; 502/324; 502/325; 502/326; 502/327; 502/328; 502/329; 502/330; 502/331; 502/332; 502/335; 502/336; 502/337; 502/338; 502/340; 502/341; 502/342; 502/343; 502/344; 502/345; 502/346; 502/349; 502/352; 502/353; 502/354; 502/355; 562/418; 562/518; 562/519; 562/520; 562/521; 562/522; 562/523; 562/524; 562/525; 562/526; 68/469.9; 68/470; 68/471

[58] Field of Search .................. 502/202, 207, 502/302–308, 310–315, 316–332, 335–338, 340–346, 349, 352–355; 568/469.9, 470, 471; 562/418, 518, 519, 520, 521, 522, 523, 524, 525, 526, 407

[56] References Cited

U.S. PATENT DOCUMENTS

| | | | |
|---|---|---|---|
| 3,746,657 | 7/1973 | Miller et al. ...................... | 502/202 |
| 4,388,223 | 6/1983 | Ferlazzo et al. .................. | 502/211 |
| 4,537,874 | 8/1985 | Sato et al. ....................... | 502/311 |

FOREIGN PATENT DOCUMENTS

| | | |
|---|---|---|
| 0000835 | 2/1979 | European Pat. Off. . |
| 342 777 | 11/1989 | European Pat. Off. . |
| 344 884 | 12/1989 | European Pat. Off. . |
| 352 023 | 1/1990 | European Pat. Off. . |
| 575 897 | 12/1993 | European Pat. Off. . |
| 33 38 380 | 4/1984 | Germany . |

Primary Examiner—Anthony Green
Attorney, Agent, or Firm—Keil & Weinkauf

[57] ABSTRACT

Catalysts of the formula I $$[A_aB_bO_x]_p [C_cD_dFe_eCo_fE_iF_jO_y]_q \qquad I,$$

where

A is bismuth, tellurium, antimony, tin and/or copper,
B is molybdenum and/or tungsten,
C is an alkali metal, thallium and/or samarium,
D is an alkaline earth metal, nickel, copper, cobalt, manganese, zinc, tin, cerium, chromium, cadmium, molybdenum, bismuth and/or mercury,
E is phosphorus, arsenic, boron and/or antimony,
F is a rare-earth metal, vanadium and/or uranium,
a is from 0.01 to 8,
b is from 0.1 to 30,
c is from 0 to 4,
d is from 0 to 20,
e is from 0 to 20,
f is from 0 to 20,
i is from 0 to 6,
j is from 0 to 15,
x and y are numbers determined by the valency and frequency of the elements other than oxygen in I, and p and q are numbers whose ratio p/q is in the range from 0.001 to 0.099, and a process for the preparation of these catalysts, their use for the ammonoxidation, oxidation or dehydrogenation of ethylenically unsaturated compounds, and a process for the ammonoxidation, oxidation or oxidative dehydrogenation of ethylenically unsaturated compounds in the presence of the novel catalysts.

4 Claims, No Drawings

CATALYST BASED ON OXIDES OF FE, CO, BI AND MO

The present invention relates to catalysts of the formula I $$[A_aB_bO_x]_p \, [C_cD_dFe_eCo_fE_iF_jO_y]_q \qquad I,$$

where
A is bismuth, tellurium, antimony, tin and/or copper,
B is molybdenum and/or tungsten,
C is an alkali metal, thallium and/or samarium,
D is an alkaline earth metal, nickel, copper, cobalt, manganese, zinc, tin, cerium, chromium, cadmium, molybdenum, bismuth and/or mercury,
E is phosphorus, arsenic, boron and/or antimony,
F is a rare-earth metal, vanadium and/or uranium,
a is from 0.01 to 8,
is b is from 0.1 to 30,
c is from 0 to 4,
d is from 0 to 20,
e is from 0 to 20,
f is from 0 to 20,
i is from 0 to 6,
j is from 0 to 15,
x and y are numbers determined by the valency and frequency of the elements other than oxygen in I, and p and q are numbers whose ratio p/g is in the range from 0.001 to 0.099.

The present invention also relates to a process for the preparation of these catalysts, to the use of these catalysts for the ammonoxidation, oxidation or dehydrogenation of ethylenically unsaturated compounds, and to a process for the ammonoxidation, oxidation or oxidative dehydrogenation of othylenically unsaturated compounds in the presence of the novel catalysts.

EP-A 000 835 describes catalysts having the composition $$[M'_{m'}N'_{n'}O'_{x'}]_{q'} \, [A'_{a'}C'_{b'}D'_{c'}E'_{d'}F'_{e'}N'_{f'}O'_{y'}]_{p'},$$

where
M' is Bi, Te, Sb, Sn and/or Cu,
N' is Mo and/or W.
A' is an alkali metal, Ti and/or Sm,
C' is Ni, Co, Mn, Mg, Be, Ca, Sr, Ba, Zn, Cd and/or Hg,
D' is Fe, Cr, Ce and/or V,
E' is P, As, B and/or Sb,
F' is a rare-earth metal, Ti, Zr, Nb, Ta, Re, Ru, Rh, Ag, Au, Al, Ga, In, Si, Ge, Pb, Th and/or U.
a' is 0–4,
b' is 0–20,
c' is 0.01–20,
d' is 0–4,
e' is 0–8,
f' is 8–16,
m' is 0.01–10,
n' is 0.1–30,
and x' and y' are numbers determined by the valency and frequency of the elements other than oxygen, and q' and p' are numbers whose ratio q'/p' is in the range from 0.1 to 10.

The component $[M'_{m'}N'_{n'}O'_{x'}]$ is referred to as the key phase, and the component $[A'_{a'}C'_{b'}D'_{c'}E'_{d'}F'_{e'}N'_{f'}O'_{y'}]$ is referred to as the guest phase.

Regarding the preparation of these catalysts, EP-A 000 835 recommends pre-forming component $[M'_{m'}N'_{n'}O'_{x'}]$ in the absence of the other constituents, and then mixing it with oxides or water-soluble salts of the elements of the guest phase and, after drying, calcining the mixture.

EP-A 000 835 furthermore discloses to employ the catalytic compositions mentioned therein as catalysts for gas-phase-catalytic oxidation of organic compounds. However, the compositions disclosed in EP-A 000 835 have the disadvantages that they do not have entirely satisfactory activity and selectivity when used in the gas-phase-catalytic oxidation of organic compounds.

DE-C 33 38 380 discloses catalytically active compositions of the formula II $$Bi_{a''}W_{b''}Fe_{c''}Mo_{d''}Y^1_{e''}Y^2_{f''}Y^3_{g''}Y^4_{h''}O_{x''} \qquad (II),$$

where
$y^1$ is nickel and/or cobalt,
$y^2$ is thallium, an alkali metal and/or an alkaline earth metal,
$Y^3$ is phosphorus, arsenic, boron, antimony, tin, cerium, lead and/or niobium,
$Y^4$ is silicon, aluminum, zirconium and/or titanium,
d' [sic] is 12,

| a' [sic] is from 0.5 to 5 | where a"/b" is |
| b" is from 0.5 to 4 | from 0.1 to 4, | c" is from 0.2 to 5,
e" is from 3 to 10,
f" is from 0.02 to 2,
g" is from 0 to 5,
h" is from 0 to 10, and
x" is a number determined by the valency and frequency of the elements other than oxygen in II,
which are obtained by first mixing a bismuth compound and a tungsten compound in an aqueous medium, drying the aqueous mixture, calcining the resultant composition at from 600° to 900° C. and subsequently powdering the product in such a way that the particle size is less than 152 μm, and treating the resultant powder with an aqueous solution of the sources of the other constituents of the composition II, and evaporating, shaping and calcining the resultant mixture.

DE-C 33 38 380 also discloses that the compositions II are suitable as catalysts for the gas-phase-catalytic preparation of unsaturated aldehydes by oxidation.

However, the compositions II disclosed in DE-C 33 38 380 have the disadvantage that they do not have entirely satisfactory activity and selectivity in the ammonoxidation of propene to acrylonitrile.

It is an object of the present invention to provide catalysts which do not have said disadvantages.

We have found that this object is achieved by the catalysts defined at the outset.

Suitable elements in the novel catalysts are:
A is bismuth, tellurium, antimony, tin and/or copper,
B is molybdenum and/or tungsten,
C is an alkali metal, thallium and/or samarium,
D is an alkaline earth metal, nickel, copper, cobalt, manganese, zinc, tin, cerium, chromium, cadmium, molybdenum, bismuth and/or mercury,
E is phosphorus, arsenic, boron and/or antimony,
F is a rare-earth metal, vanadium and/or uranium,
a is from 0.01 to 8, preferably from 0.1 to 6,
b is from 0.1 to 30, preferably from 0.2 to 8,
c is from 0 to 4, preferably from 0.01 to 3,
d is from 0 to 20, preferably from 0 to 15,
e is from 0 to 20, preferably from 0 to 15,
f is from 0 to 20, preferably from 0 to 15,
i is from 0 to 6, preferably from 0 to 4,
j is from 0 to 15, preferably from 0 to 10.

Preferred catalysts are those which contain at least one of the elements bismuth, molybdenum and/or tungsten and iron having a stoichiometric coefficient which is not zero and is preferably ≧0.01.

Furthermore, the novel catalysts I prove to be more advantageous the higher the percentage of the various chemically different components having a mean particle size (measured using a Sympatec laser diffraction instrument) in the range from 10 nm to less than 1 μm, preferably in the range from 10 nm to 800 nm, particularly preferably from 10 nm to 600 nm.

In particular, particles of the key phase and/or of the guest phase of the catalyst preferably have a mean particle size in the range from 10 nm to less than 1 μm, particularly preferably in the range from 10 nm to 800 nm, very particularly preferably from 10 nm to 600 nm.

The key phase $A_aB_bO_x$ here preferably has the stoichiometry $$Bi_2W_2O_9 \text{ and/or } Bi_2Mo_2O_9,$$

the former being preferred.

The novel compositions are obtainable by the following steps:
(a) preparation of a key phase having the composition $A_aB_bO_x$,
(b) preparation of a guest phase having the composition $C_cD_dFe_eCo_fE_iF_jO_y$, or water-soluble salts of elements of the guest phase or a mixture of at least one water-soluble salt of these elements and at least one calcined phase of one of these elements which is not in the form of a water-soluble salt, and
(c) mixing of the key phase with the guest phase, and
(d) if desired drying of the mixture obtained in (c), followed by calcination and, if desired, shaping of the catalyst composition formed in this way in a manner known per se (see EP-A 000 835 and DE-C 33 383 80).

In a particular embodiment, at least one of the catalyst components (the key phase, the precursor thereof, the guest phase or a calcined oxide phase of one of the compounds occurring in the guest phase) is comminuted by means known per se, for example using a ball mill or by jet grinding, wet comminution being preferred. The mean particle size achieved by the comminution is preferably chosen to be in the range from 10 nm to less than 1 μm, particularly preferably from 10 nm to 800 nm, very particularly preferably from 10 nm to 600 nm.

The comminuted catalyst component is then usually mixed with the remaining catalyst components, if desired likewise comminuted, preferably in solution or suspension.

The resultant mixture is generally subjected to drying, preferably spray drying to give a spray material.

The resultant catalyst precursor is then generally calcined at from 400° to 900° C., preferably at from 500° to 800° C., preferably in a stream of air. The calcination is generally carried out for from 0.1 to 20 hours.

The catalytically active composition is preferably applied to an oxidic support, such as $SiO_2$, $Al_2O_3$, $TiO_2$ or $ZrO_2$. In a preferred embodiment, the oxidic support, such as $SiO_2Al_2O_3$, $TiO_2$ or $ZrO_2$ is, before the spray drying, mixed [lacuna] the mixture of catalyst components, it being possible to employ the catalyst prepared in this way directly for organic syntheses in a fluidized-bed reactor.

Furthermore, the calcined catalyst can be comminuted and shaped in a manner known per se, for example by pressing hollow cylinders or extrudates by methods known per se.

In a further preferred embodiment, the precursor of the key phase, $[A_aB_bO_x]$, is comminuted after calcination, preferably at from 400° to 900° C., usually in a stream of air. The calcination in generally carried out for from 0.1 to 20 hours.

A very intimate, preferably finely divided, dry mix of the other constituents of the novel catalyst desired is generally prepared starting from sources suitable in a manner known per se (cf. EP-A 835 and DE-C 33 38 380) (for example water-soluble salts, such as halides, nitrates, acetates, carbonates or hydroxides, are combined in an aqueous solution, and the aqueous solution is subsequently spray-dried, or water-insoluble salts, for example oxides, are suspended in an aqueous medium and the suspension is subsequently spray-dried); the dry mix is referred to here as the precursor of the guest phase. The only essential feature is that the constituents of the preguest phase are either already oxides or are compounds which can be converted into oxides by heating, if necessary in the presence of oxygen.

The calcined precursor of the key phase and the precursor of the guest phase are subsequently usually mixed with one another in the desired mixing ratio, preferably compacted by pressing and then expediently calcined (normally in a stream of air) at from 400° to 900° C. for a number of hours.

In the case of unsupported catalysts, the pressing is generally carried out directly to the desired catalyst geometry, preference being given to hollow cylinders having an external diameter and length of from 2 to 10 mm and a wall thickness of from 1 to 3 mm. However, the active catalysts according to the invention can also be comminuted after the calcination and applied to inert supports in order to prepare supported catalysts. The application can also have already been carried out before the final calcination. In this case, the application is preferably carried out as described in EP-B 293 859. It is of course also possible to employ the compositions according to the invention in powder form.

The catalysts according to the invention have, compared with corresponding catalysts of the prior art, both an increased activity and an increased selectivity for gas-phase-catalytic oxidation of organic compounds, such as lower (3 to 6 carbon atoms) alkanes, alkanols, alkanals, alkenes and alkenals, to olefinically unsaturated aldehydes and/or carboxylic acids and to the corresponding nitriles (ammonoxidation), in particular of propene to acrylonitrile and of i-butene or tert-butanol to methacrylonitrile. They are also suitable for the oxidative dehydrogenation of organic compounds.

EXAMPLES

Example 1

(a) Preparation of a key phase 0.5 kg of a solution of $Bi(NO_3)_3$ in aqueous nitric acid (11% by weight of Bi, 6.4 % by weight of $HNO_3$, in each case based on the solution) was mixed with 67 g of $H_2WO_4$, and the mixture was stirred at 50° C. for 1 hour.

The resultant suspension was spray-dried at 290° C. and calcined at 750° C. for 2 hours. The resultant preformed calcined mixed oxide ($Bi_2W_2O_9$) containing a small amount of $WO_3$ impurity was subsequently wet-comminuted to a mean particle size of 400 nm (measured on a Sympatec laser diffraction instrument) by means of a stirred mill, giving suspension 1 (precursor of key phase 1).

(b) Preparation of a guest phase

A solution of 5.57 kg of ammonium heptamolybdate in 16 l of water was mixed with a solution containing 3.83 kg of cobalt(II) nitrate and 2.66 kg of iron(III) nitrate dissolved in 8 l of 10% strength by weight nitric acid, and with 19.1 kg of an aqueous mixture containing 49% of its weight of colloidal $SiO_2$, and 15.4 g of an aqueous solution containing 48% by weight of KOH (suspension 2).

Suspension 1 was subsequently mixed with suspension 2. The mixture was then evaporated to dryness by spray drying and subsequently calcined at 290° C. for 3 hours, then at 425° C. for a further 3 hours and finally at 610° C. for a further 3 hours. The resultant catalyst was suitable for direct use in a fluidized-bed reactor.

The catalyst had the following composition:

$[Bi_2W_2O_9]_{0.05}[Mo_{12}Co_5Fe_{2.5}K_{0.05}O_x]$

Example 2

Comparative catalyst (analogous to Example 1 of EP-A 000 835)

Example 1 was repeated, but with the difference that the precursor of the key phase was employed directly after spray drying without prior comminution.

Example 3

Ammonoxidation of propene (a) A propene/ammonia/air/water gas mixture in the volume ratio 1/1.3/10/4.7 was reacted at 450° C. in a fixed-bed reactor. The contact time (volume (gas)/volume-(catalyst) per unit time) was 4.5 seconds. The catalyst employed was the catalyst from Example 1.

(b) Example 3(a) was repeated using the with [sic] catalyst from Example 2.

The results of the ammonoxidation are shown in the table below.

TABLE

| Catalyst | Propene conversion [%] | Yield [mol %] | Selectivity [%] |
|---|---|---|---|
| Example 1 for comparison | 98.5 | 85.8 | 87.1 |
| Example 2 | 98.1 | 82.2 | 83.8 |

We claim:
1. A catalyst of the formula I

$(A_aB_bO_x)_p (C_cD_dFe_eCo_fE_iF_jO_y)_q$   I, where
A is bismuth, tellurium, antimony, tin and/or copper,
B is molybdenum and/or tungsten,
C is an alkali metal, thallium and/or samarium,
D is an alkaline earth metal, nickel, copper, cobalt, manganese, zinc, tin, cerium, chromium, cadmium, molybdenum, bismuth and/or mercury,
E is phosphorus, arsenic, boron and/or antimony,
F is a rare-earth metal, vanadium and/or uranium,
a is from 0.01 to 8,
b is from 0.1 to 30,
c is from 0 to 4,
d is from 0 to 20,
e is from 0 to 20,
f is from 0 to 20,
i is from 0 to 6,
j is from 0 to 15,
x and y are numbers determined by the valency and frequency of the elements other than oxygen in I, and p and q are numbers whose ratio p/q is in the range from 0.001 to 0.099,
obtained by the following steps
(a) preparation of a key phase having the composition $A_aB_bO_x$,
(b) preparation of a guest phase having the composition $C_cD_dFe_eCo_fE_iF_jO_y$ or water-soluble salts of elements of the guest phase or a mixture of at least one water-soluble salt of the elements of the guest phase and at least one calcined phase of one of the elements of the guest phase which is not in the form of a water-soluble salt, and
(c) mixing of the key phase with the guest phase, and
(d) optionally drying the mixture obtained in (c), optionally drying the mixture obtained in (c), optionally followed by calcination and optionally followed by shaping of the catalyst composition
the mean particle size of at least one of a guest phase or a key phase composition being in the range from 10 nm to less than 1 µm.

2. A catalyst as defined in claim 1, wherein the catalyst has been applied to an oxidic support material.

3. A process for the preparation of a catalyst as defined in claim 1 in which a key phase and a guest phase are prepared, the two phases are mixed and subsequently, the mixture of these phases is calcined, wherein the key phase has the composition $A_aB_bO_x$ and the guest phase has the composition $C_cD_dFe_eCo_fE_iF_jO_y$.

4. A process for the ammonoxidation, oxidation or oxidative dehydrogenation of ethylenically unsaturated compounds wherein the process is carried out using a catalyst as defined in claim 1.

* * * * *